US005584808A

United States Patent [19]
Healy

[11] Patent Number: 5,584,808
[45] Date of Patent: Dec. 17, 1996

[54] VALVE MECHANISM

[76] Inventor: Patrick M. Healy, 401 N. Roosevelt, Wichita, Kans. 67208

[21] Appl. No.: 492,835

[22] Filed: Jun. 20, 1995

[51] Int. Cl.$^6$ ..................................... A61M 5/00
[52] U.S. Cl. .............. 604/86; 604/88; 604/283; 604/905; 604/249
[58] Field of Search ..................... 604/283, 247, 604/249, 201–206, 256, 164, 167, 169, 905, 86–88

[56] References Cited

U.S. PATENT DOCUMENTS 5,062,836 11/1991 Wendell ............................ 604/249 X
5,242,393 9/1993 Brimhall et al. .................... 604/283 X
5,350,362 9/1994 Stouder, Jr. ......................... 604/247 X Primary Examiner—John D. Yasko
Attorney, Agent, or Firm—Richard K. Thomson

[57] ABSTRACT

A valve which can be used to facilitate needleless transfer of medication from the container to a patient. A slidable actuator is engaged by the nozzle portion of a syringe and the tapered lead portion of the slide is forced into the container through a pre-slit elastomeric membrane. The membrane is relatively thick, preferably between 25 and 75% the width dimension of the membrane and, more preferably, between 40 and 50% of that dimension. The thick membrane is durable enough to withstand repeated usage and damage resistant enough to permit use with needled syringes.

4 Claims, 5 Drawing Sheets

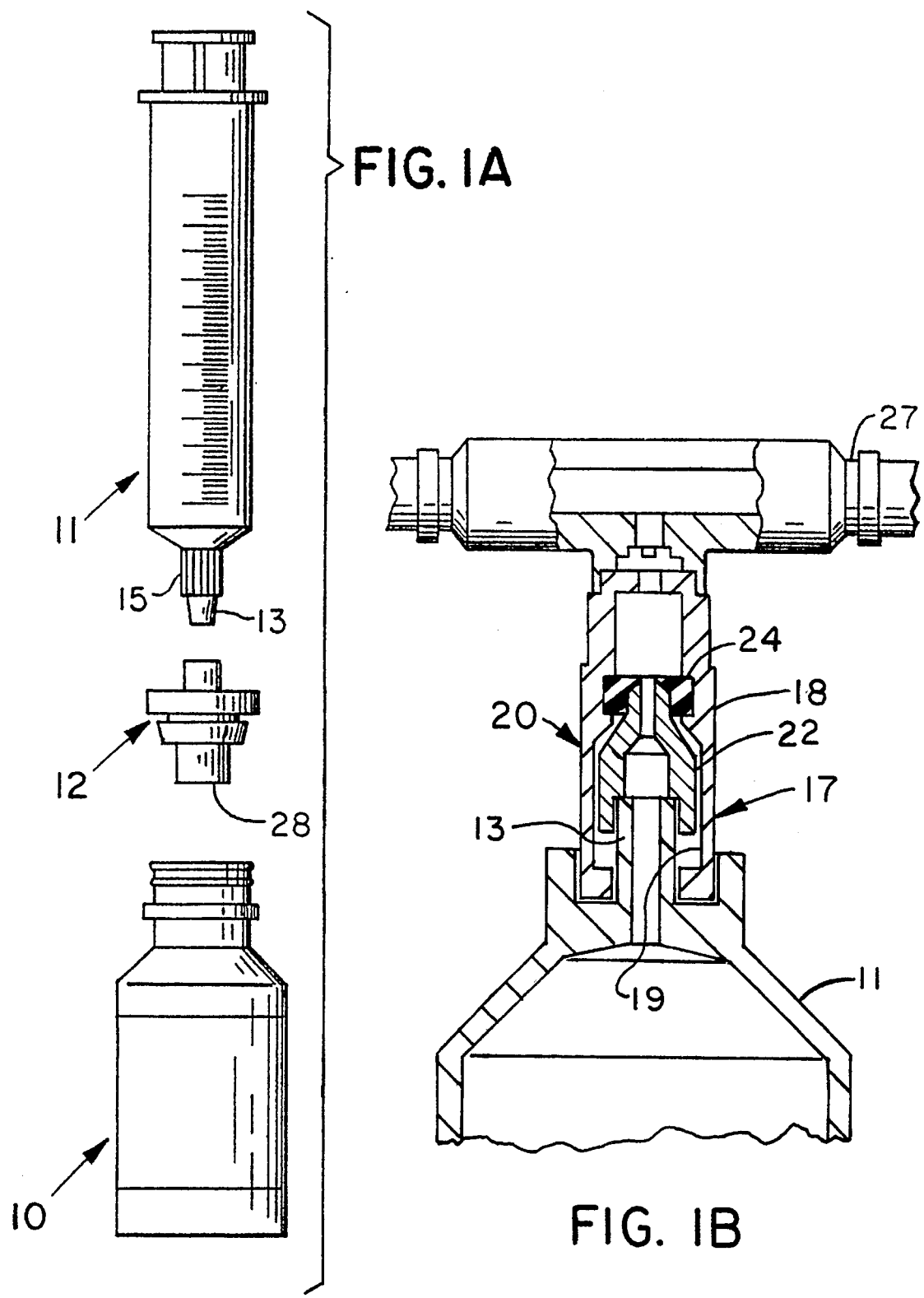

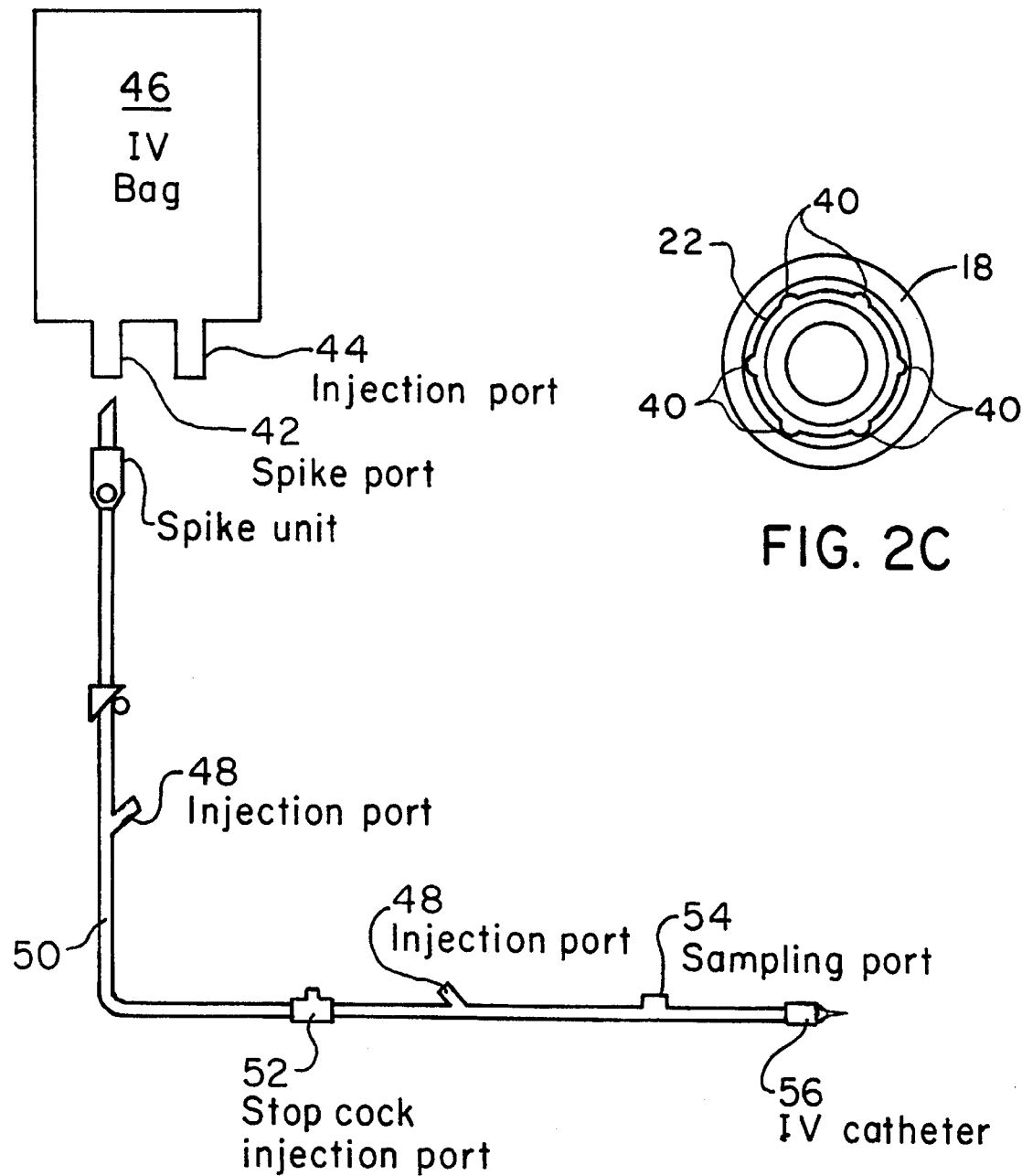

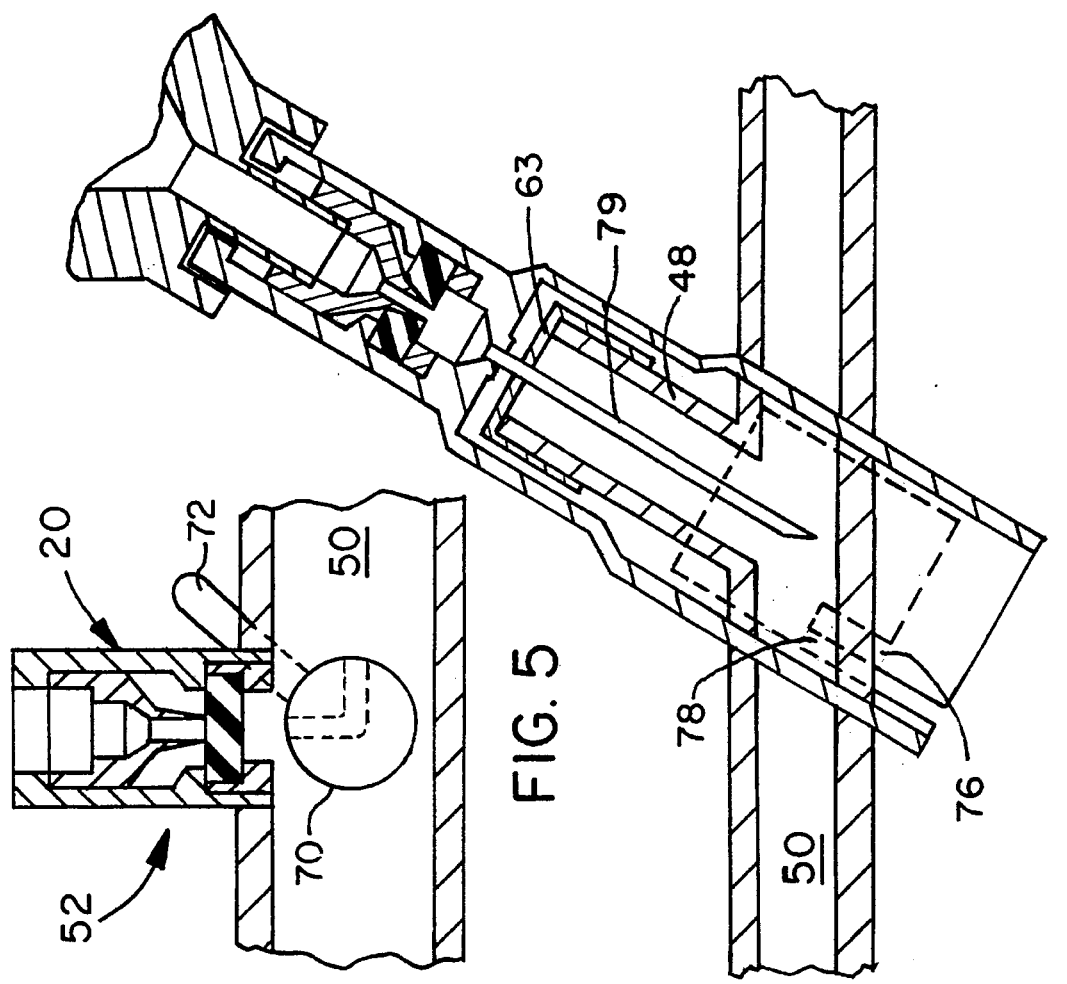
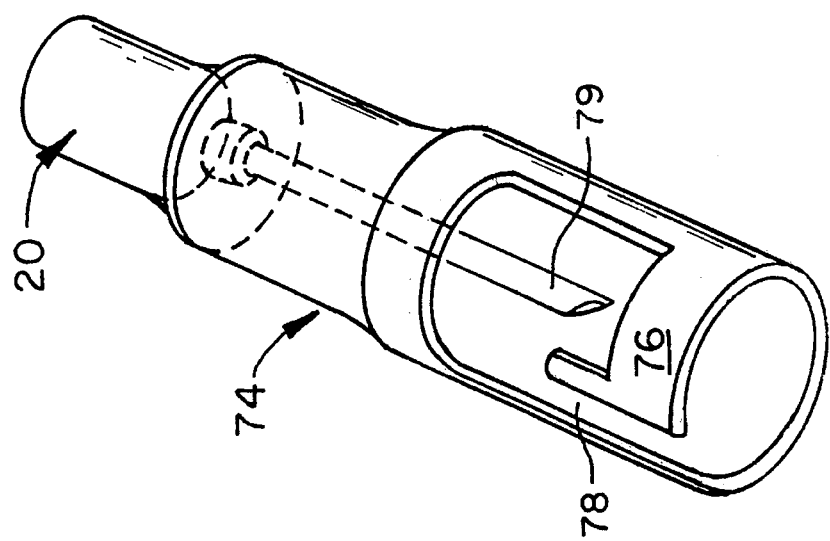

5,584,808

VALVE MECHANISM

FIELD OF THE INVENTION

The present invention is directed to the field of valves used to dispense or receive medication. More specifically, the present invention is directed to an improved valve configuration for use in a variety of applications including the medication container described and claimed in U.S. Pat. No. 5,092,840. The present application is a continuation-in-part of U.S. patent application Ser. No. 08/025,990 entitled "Valved Medication Container", which issued as U.S. Pat. No. 5,425,465 Jun. 20, 1995.

BACKGROUND AND SUMMARY OF THE INVENTION

Recent articles in medical journals demonstrate the hidden costs of using needles to administer medication to patients, and the like. One article reports that fully one third of all work-related hospital accidents relate to needlesticks. Needle stick injuries have a potential devastating long term impact on hospital workers with the increasing risks of blood-borne disease transmission, particularly diseases such as human immunodeficiency virus (HIV) and hepatitis B. That same article reports needle stick injury rates in excess of one per ten employees. A second article determined the average cost (not including costs associated with employee loss due to debilitating injury) to be $405 per injury. These costs are in addition to the known costs associated with the purchase and disposal of the needled devices.

A third article reports the hospital handling of needles leading to needle stick injuries as being 1) intramuscular or subcutaneous injections,
2) intravenous catheters,
3) disassembly of the needled devices,
4) recapping attempts,
5) multistep procedures (e.g., multi-component medication mixing),
6) disposal of needles.

This same article reported that only 18% of the needle stick injuries involved in this study could be addressed by an improved disposal technique and concluded that only a portion of those 18% could be eliminated by such improved handling techniques. This article suggests the answer lies in eliminating the unnecessary use of needled devices, that is, usage of needleless and protected needle devices is encouraged.

The risks associated with using needles and the advantages of needleless transfer systems for medication are further detailed in U.S. Pat. No. 5,092,840, which is hereby incorporated by reference. The significant reduction of the risk of transmitting blood-borne diseases make the use of such a needleless system very attractive. Still, it is important that the valve used with various medications be workable without exacting a substantial penalty in the area of cost. To this end, the present invention presents a particular workable, cost-effective valve mechanism.

The present valve mechanism includes a slidable member that is engaged and operated by the blunt end of a needleless syringe which engages a slit in a relatively thick elastomeric membrane to force open a passageway that permits medication to be withdrawn. This valve can be provided with an optional vent passage that may be equipped with a one-way valve to avoid medication leakage. The vent passageway may be required in some applications requiring larger valves.

It will be appreciated that although the advantages of a needleless transfer system will be readily apparent to a majority of the members of the medical profession, there will be some practitioners that may, for certain applications, wish to continue to utilize needles. It is therefore important that the valve which may be utilized to successfully introduce a needleless transfer system be capable of being operated by a needle, as well.

This valve will be used in a number of applications requiring multiple repeated uses. It will, therefore, be important that the valve membrane be capable of resealing and that it be durable to standup to this repeated usage. The pre-slit, thick membrane employed with the present valve mechanism has several advantages over a relatively thin membrane. First, the thick membrane does reseal preventing the flow of both air and fluid into and out of the valve. Second, the thick design is more durable, able to withstand the wear and tear of repeated uses. Lastly, it will be appreciated the thick membrane will be less likely to be cut and disintegrated by the point of a needle. Such damage to the membrane would be undesirable, not only from the standpoint of the integrity and operability of the valve, but from the perspective of contaminating the medicine with particles which break off from the valve.

The slidable member has a tapering leading end to facilitate insertion with a rounded tip portion to reduce the wear and tear on the membrane. Further, the present valve can easily be employed with a needle during transitional usage, that is, use during the transition period necessary for needleless systems to gain widespread acceptance. The internal surface of the slide which has a tapered portion designed to engage and grip the lead end, or nozzle, of a needleless syringe, will serve to guide the needle to the pre-formed slit, avoiding unnecessary penetration of the membrane which could result in deterioration.

In defining the term "relatively thick", Applicant has determined a range of thicknesses, as they relate to the diameter of the membrane, of between 25 and 75%, and more preferably, between 40 and 50% of the membrane diameter, provides acceptable performance.

Various other features, advantages and characteristics of the present invention will become apparent after a reading of the following specification.

BRIEF DESCRIPTION OF THE DRAWINGS

FIG. 1A is an exploded schematic showing three of the elements of the needleless transfer system made possible by the valve of the present invention;

FIG. 1B is a side view in partial section depicting the needleless syringe of the present invention engaging a fourth element of the present needleless transfer system;

FIG. 1C is a schematic side view of an IV system showing a variety of applications which can utilize the valve of the present invention;

FIG. 2C is an end view of the valve mechanism of the present invention;

FIG. 5 is a cross-sectional side view of the valve of the presents invention incorporated into a stop cock of an IV line;

FIG. 6 is a perspective view of an attachment for an IV port incorporating the valve of the present invention; and FIG. 7 is a cross-sectional side view showing the attachment of FIG. 6 installed.

DETAILED DESCRIPTION OF THE PREFERRED EMBODIMENTS

Figure 2A:
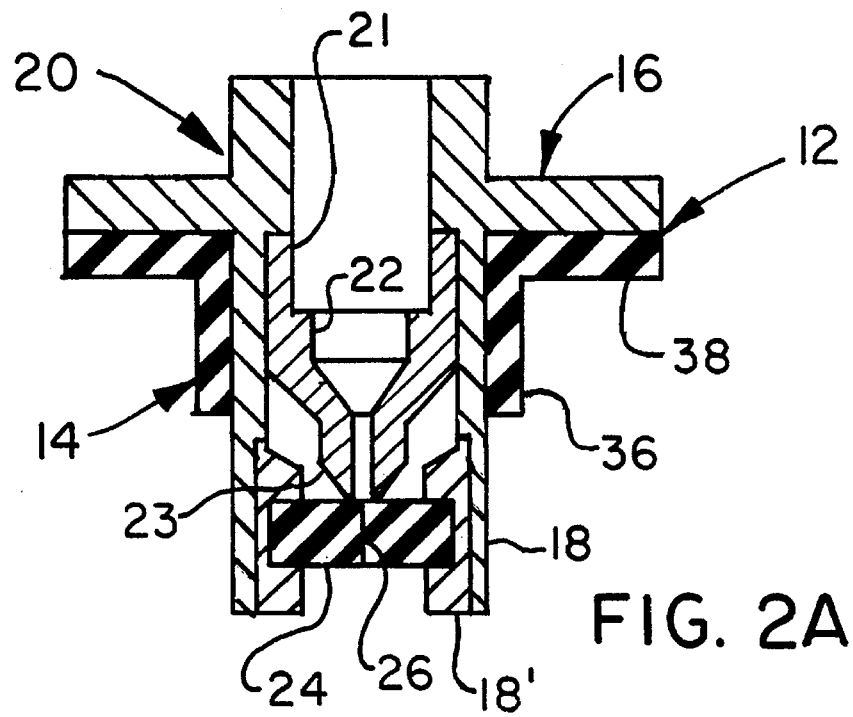
FIG. 2A is a cross-sectional side view of the preferred embodiment of the valve element actuated by the nozzle of a syringe.

FIG. 1A depicts three elements of the needleless transfer system made possible by the valve of the present invention, medication container 10, valved stopper 12, and needleless syringe 11, with the fourth element, injection port 17 connected to an IV tube 27, being shown in FIG. 1B. Valved stopper 12 has a member which has been designed to be engaged and actuated by blunt, tubular nozzle portion 13 of needleless syringe 11. FIG. 1B depicts nozzle portion 13 with luer being received within neck 19 of injection port 17.

The key element of this needleless transfer system is the valve 20. It is important that this component work effectively but be capable of being manufactured inexpensively. Health and safety of hospital workers is of vital importance, but if they come with too high a price tag, the resistance to change, coupled with inertia, may be too great for a new system to overcome. Further, in order to deal with the inertia problem, it is important that the system chosen to initiate widespread usage of needleless systems be capable of usage with conventional needle-bearing syringes. Accordingly, the bulk of this description is directed to detailing the features and characteristics of valve 20 which is a highly economic system having the desired characteristics.

Figure 2B:
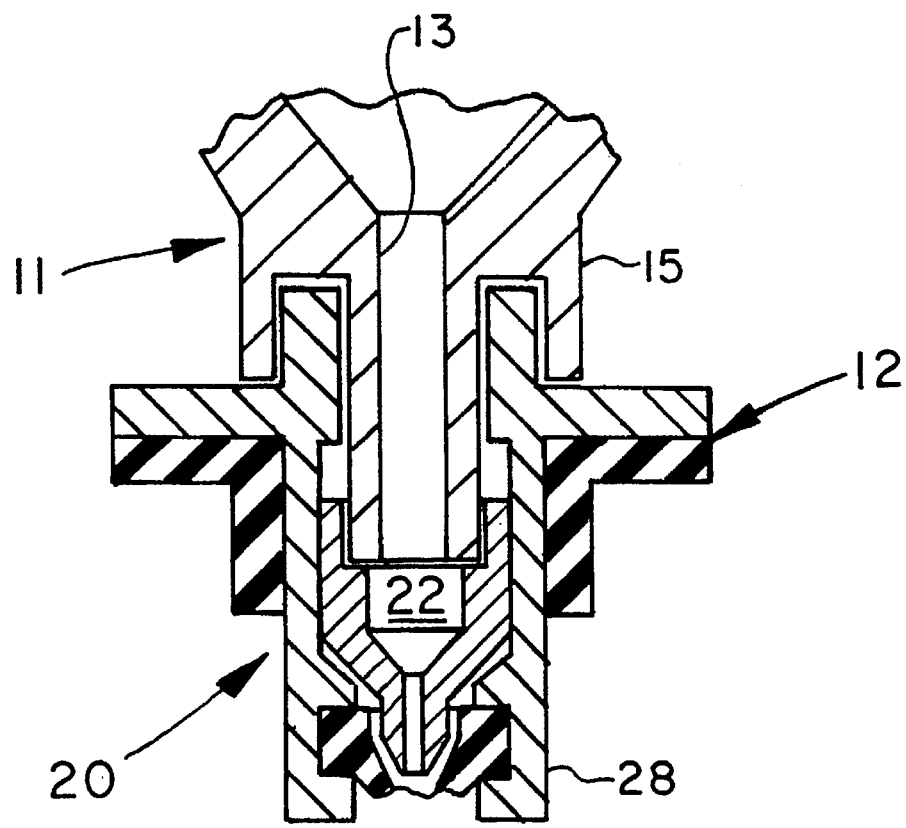
FIG. 2B is a cross-sectional side view of the preferred embodiment of the valve element actuated by the nozzle of a syringe.

A first preferred embodiment of valve 20 is shown in FIGS. 2A–C. In these Figures, valve 20 is depicted as part of a stopper 12 for a medication container. It will be appreciated that for other applications, the valve will be housed in a simple cylindrical sleeve which may be formed as an integral part of the element with which it operates or as a separate element that can be connected to the element (i.e., retrofit).

This stopper 12 includes a first outer member 14 having a first portion 36 shaped to fit snugly within bottle 10 and flange 38 to overlie the mouth of container 10 and a second inner member 16 which contains the operative valve element 20. Preferably, the first outer member 14 is made of an elastomer and may be provided with a protruding ridge (not shown) to improve sealing within container 10 and the inner member 16 is made of a moldable plastic material. Inner member 16 is most preferably made of two portions 18 and 18' which may be bonded together, for ease of assembly. Valve assembly 20 includes actuator 22 slidably mounted within inner member 16 and an elastomeric membrane 24 whose outer periphery is fixed with respect to inner member 16 and has a pre-formed slit 26 therethrough.

Membrane 24 is regarded as relatively thick, that is, having a larger than normal thickness to diameter ratio. It is preferred that the thickness fall in the range of between 25 and 75% of the membrane diameter and more preferably, in the 40 to 50% range. One exemplary membrane 24 had a thickness which calculated to be 30% of its diameter in the preinstalled condition, but once inserted into the housing 18 and radially compressed, computed to be more on the order of 40% of its diameter. Slit 26 is normally closed and, in the closed position, prevents egress of medication and ingress of air or other fluids. Sliding of actuator 22 may be facilitated by a coating of Teflon® polymer, or the like on one of the relatively slidable elements or by forming contact-reducing ribs 40 on one of the contacting surfaces. By way of example, FIG. 2C depicts the external surface of slide 22 as having six protrusions which reduce the surface area contact with element 18 thereby resulting in reducing the frictional resistance to movement.

As shown in FIG. 2B, nozzle portion 13 of needleless syringe 11 is received in the trailing end 21 of actuator 22 and is advanced such that leading end 23 pushes through slit 26. Trailing end 21 is sized such that nozzle 13 has an interference fit therewith. In this embodiment, slit 26 may merely be a short longitudinal cut through the thick membrane 24, although more elaborate designs may be used, as well. Leading end 23 of actuator 22 causes the elastomer to bulge as it forces its way through. When syringe 11 has a proper dosage of medication, withdrawal of nozzle portion 13 from neck 19 of container 10 will provide a retraction force on actuator 22 as a result of the interference fit with trailing end 21, which coupled with the restoring force of elastomeric membrane 24 acting against the tapered surface of leading end 23, will return actuator 22 to its at rest position (FIG. 2A). Should the combination of these forces prove inadequate in certain applications, any of a variety of restorative spring members (not shown) can be used.

Figures 3, 4:
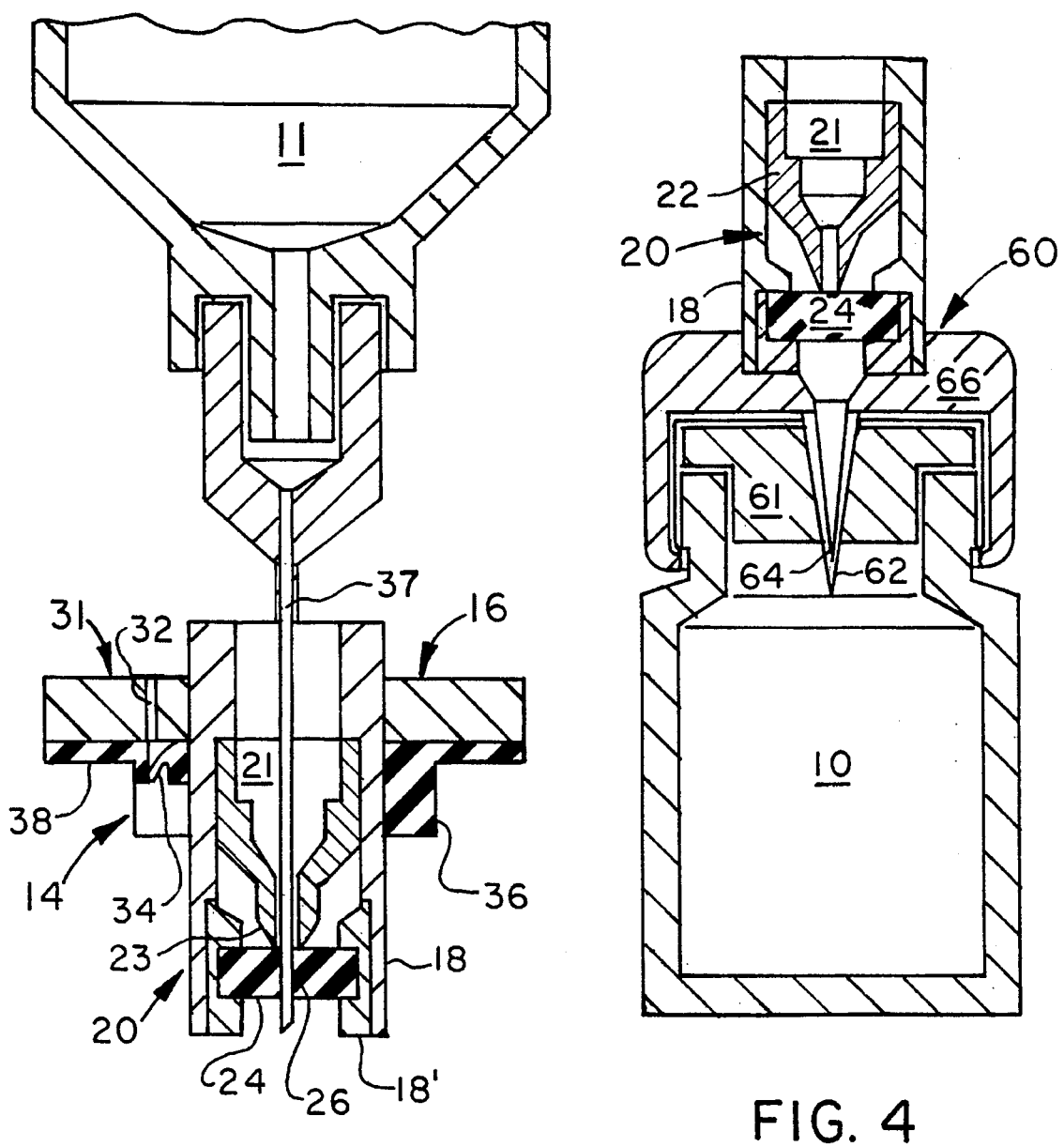
FIG. 3 is a cross-sectional side view of a stopper employing the valve of the present invention which is equipped with an air vent.
FIG. 4 is a cross-sectional side view of a trocar unit for use with a medication bottle.

Depicted in FIG. 3 is an air vent 30. Air vent 30 includes a hole 32 through inner member 16 and a molded flapper valve 34 formed in outer elastomeric member 14. Flapper valve 34 is a one-way valve which prevents medication from flowing out but permits the influx of air to aid in medication withdrawal by syringe 11. Such a feature may be required on the larger containers 10 to permit adequate passive insufflation for medication withdrawal. Passive insufflation is contrasted with the forced insufflation initiated by the syringe during normal withdrawal procedures. It should be noted that one of the benefits of the valved container 10 made possible by the valve of the present invention is the provision of multiple-dose containers which can significantly reduce the per administration cost of medication to the patient. It will be appreciated that many of the other applications for the valve of the present invention (particularly those involving only injections), will not require air vents.

Also depicted in FIG. 3 is the use of the valve 20 of the present invention with a needled syringe. Needle 37 will be guided by tapering surfaces of slide 22 to slit 26. The opening in leading end 23 of slide 22 will preferably accommodate up to an 18 gauge needle. Thick membrane 24 will resist puncturing by needle 37 and will, therefore, not easily be broken into pieces as might occur with a thinner membrane.

FIG. 4 depicts a trocar unit 60 employing the valve design of the present invention which may be affixed to a conventional medication container 10 by axially pushing spike 62 through conventional stopper 61 establishing a passageway between opening 64 and valve member 20. In this manner, the valve 20 of the present invention can be retrofit onto any current medication container. Plastic cap 66 which may be integrally molded with housing 18 of valve 20, will snap over the mouth of bottle 10.

A number of the possible uses for the valve of the present invention are depicted in FIG. 1C. Valve 20 of the present invention could be utilized in both the spike port 42 and injection port 44 of the IV bag 46, at each of the injection ports 48 of the IV tube 50, the stop cock injection port 52 of the IV line 50 (:as discussed in detail below), the sampling port 54, and the IV needle 56 itself. As alluded to earlier, each element may be premanufactured with the valve 20 built into it, or the valve mechanism 20 may be retrofit using a clip on element.

FIG. 5 depicts the valve 20 of the present invention incorporated into an IV line stop cock 70. Stop cock 70 has a handle 72 which may be positioned in either of two positions to direct the injected flow primarily upstream or down, as may be desired.

FIG. 6 shows a trocar unit 74 which can be connected to any of the injection ports 44 of the IV line. Spring finger 76 created by J-slot 78 can snap around IV line 50 and secure trocar unit in place over injection port 48 after needle 78 has penetrated the port cover membrane 63 (see FIG. 7). As mentioned earlier, while it would be preferable to form the valve mechanism 20 as an integral part of each element with which it is to be used, the use of these snap on devices permits the present valve to be used with existing equipment by a retrofit technique.

Various changes, alternatives and modifications will become apparent to a person of ordinary skill in the art following a reading of the foregoing specification. It is intended that all such changes, alternatives and modifications as fall within the scope of the appended claims be considered part of the present invention.

What is claimed is:

1. A valve mechanism particularly useful in transferring medication from a container to a patient by means of an IV injection tube or the like, said valve mechanism comprising:
   a) a first cylindrical housing;
   b) an elastomeric membrane captured within said housing and including
      i) a longitudinally extending throughbore in the form of a preformed slit;
      ii) a thickness dimension which is in a range of between 25 and 75% of its width;
   c) a slide element received within said housing including
      i) a first relatively blunt, tapered end for engaging said elastomeric membrane;
      ii) a second open end for receiving a nozzle portion of a syringe, or the like, to actuate said slide element from a first at rest position to a second engaged position which opens said pre-formed slit to permit liquid to flow therethrough;
      iii) a longitudinal throughbore formed in said first end capable of receiving a needle of a particular gauge;
      iv) a plurality of semi-cylindrical ridges formed on the exterior portion thereof to reduce surface area engagement between said slide element and an interior portion of said housing;

whereby said elastomeric membrane will restore said slide element to its first at rest position following release of pressure exerted by said syringe by exerting a restorative force against said slide element.

2. The valve mechanism of claim 1 wherein said restorative force is comprised of a component resulting from the elastomeric membrane's seeking to return to its at rest position and from a gripping force exerted by said slide element on said nozzle portion of said syringe.

3. The valve mechanism of claim 1 wherein said thickness dimension more preferably falls in the range between 40 and 50% of its diameter.

4. A valve mechanism comprising:
   a) a first cylindrical housing;
   b) a relatively thick elastomeric membrane captured within said housing and including
      i) a longitudinally extending throughbore in the form of a preformed slit;
      ii) a thickness dimension which is at least 40% of its width in its installed position;
   c) a slide element received within said housing including
      i) a first relatively blunt, tapered end for engaging said elastomeric membrane;
      ii) a second open end for receiving a nozzle portion of a syringe, or the like, to actuate said slide element from a first at rest position to a second engaged position which opens said pre-formed slit to permit liquid to flow therethrough;
      iii) a longitudinal throughbore formed in said first end capable of receiving a needle of a particular gauge;

whereby said relatively thick elastomeric membrane will restore said slide element to its first at rest position following release of pressure exerted by said syringe by exerting a restorative force against said slide element and will, by virtue of its relatively large thickness, prevent egress of fluid and ingress of air.

* * * * *